US00PP13091P2

(12) United States Plant Patent
Crowther et al.

(10) Patent No.: US PP13,091 P2
(45) Date of Patent: Oct. 15, 2002

(54) LAVANDULA PLANT NAMED 'WALVERA'

(75) Inventors: Albert Timothy Alan Crowther, Arundel (GB); David Ralph Tristram, Arundel (GB)

(73) Assignee: David Tristram, Arundel (GB)

( * ) Notice: Subject to any disclaimer, the term of this patent is extended or adjusted under 35 U.S.C. 154(b) by 0 days.

(21) Appl. No.: 09/804,916

(22) Filed: Mar. 13, 2001

(65) Prior Publication Data

US 2002/0133856 P1 Sep. 19, 2002

(51) Int. Cl.[7] ..... A01H 5/00
(52) U.S. Cl. ..... Plt./226
(58) Field of Search ..... Plt./226

(56) References Cited

PUBLICATIONS

UPOV–ROM GTITM Computer Database, 2001/04 GTI Jouve Retrieval Software, citation for 'Walvera'.*

* cited by examiner

*Primary Examiner*—Bruce R. Campell
*Assistant Examiner*—Susan B. McCormick

(57) ABSTRACT

A new cultivar of *Lavandula angustifolia* plant named 'Walvera' that is characterized by variegated foliage with gray-green centers and cream-white margins, a mounded, semi-open habit, and compact violet-blue flower spikes. In combination, these traits set it apart from all other existing varieties of Lavandula.

3 Drawing Sheets

BOTANICAL CLASSIFICATION

*Lavandula angustifolia.*

VARIETY DENOMINATION

'Walvera'.

BACKGROUND OF THE INVENTION

The present invention relates to a new and distinct cultivar of *Lavandula angustifolia* and hereinafter referred to by the cultivar name 'Walvera'. The new cultivar is a naturally occuring branch sport of *Lavandula angustifolia* 'Vera' (unpatented) and was discovered jointly by the inventors in a cultivated area of West Sussex, United Kingdom in 1993.

The new lavender plant 'Walvera' is distinct and unique due to its mounding, semi-open habit, gray-green leaves with cream-white marginal variegation, and violet-blue flowers. The closest comparison is the parent plant *Lavandula angustifolia* 'Vera' (unpatented). 'Walvera' is distinguishable from the parent plant, and all other existing varieties, by its variegated foliage.

The new invention was first asexually propagated by cuttings in West Sussex, United Kingdom by the inventors in 1995. Since that time subsequent generations have been determined fixed and stable.

SUMMARY OF THE INVENTION

The new lavender 'Walvera' is distinguished from all other known varieties of Lavandula, by the following characteristics:

1. Leaves with gray-green centers and cream-white variegated margins.
2. A mounded, semi-open habit.
3. Short, compact flower spikes of violet-blue flowers.

These unique traits set 'Walvera' apart from all other existing varieties.

BRIEF DESCRIPTION OF THE DRAWINGS

The accompanying color photographs illustrate the distinguishing characteristics of the new cultivar 'Walvera'.

Sheet 1 shows the entire plant from a side view perspective, illustrating the plant habit.

Sheet 2 illustrates the flowers on 'Walvera'.

Photo 3 is a comparative photo illustrating the variegated foliage of 'Walvera' on the left, and the foliage of the parent plant *Lavandula angustifolia* 'Vera' (unpatented) on the right. All photographs are taken using conventional photographic techniques and although foliage colors may appear different from actual colors due to light reflectance, they are as accurate as possible by conventional photography.

BOTANICAL DESCRIPTION OF THE PLANT

The following is a detailed description of the *Lavandula angustifolia* cultivar named 'Walvera'. Data was collected in Arroyo Grande, Calif. from 12 month old plants grown in one-gallon containers. Phenotypic differences may be observed with variations in environmental, climatic, and cultural conditions, without however, any difference in genotype. Color determinations are in accordance with The 1995 Royal Horticultural Society Colour Chart except where general color terms of ordinary dictionary significance are used. The growing requirements are similar to the species and no disease problems have been observed.

Botanical classification: *Lavandula angustifolia* 'Walvera'.
Common name: Lavender.
Parentage: A naturally occuring branch sport of *Lavandula angustifolia* 'Vera'.
Type: Aromatic perennial shrub.
Use: Ornamental, hedge or back of border plant.
Growth rate: 4 to 10 cm per month.
Habit: Mounded and semi-open with erect, ascending flower spikes.
Height: 1 m in height.

Spread: 0.6 m in width.
Hardiness: Zone 5 to zone 10.
Propagation method: Cuttings.
Root system: Fibrous.
Soil: Plant in well-drained soil.
Light levels: Plant in full sun.
Special needs: None observed.
Time to initiate roots: 21 to 36 days from an unrooted cutting.
Time to develop in a one-gallon container: 6 months from a rooted cutting.
Branching habit: Erect, upright and semi-open.
Seasonal interest: Violet-blue flowers in July and August.
Stem:
*Shape*.—Cylindrical.
*Surface*.—Puberulent.
*Color*.—197A,B.
*Size*.—3–5 mm in diameter, 5–20 cm in length.
Foliage:
*Arrangement*.—Erect stems of basal leaves.
*Leaf division*.—Simple.
*Apices*.—Acute.
*Base*.—Attenuate.
*Margins*.—Entire and mostly revolute.
*Leaf shape*.—Linear.
*Color of mature leaves* (*upper and low surfaces*).—Center 190A to 191A and margins 11C.
*Color of young leaves* (*lower surfaces*).—Center 189B and margins 11D.
*Color of young leaves* (*upper surfaces*).—189D.
*Upper and lower surfaces*.—Puberulent.
*Venation*.—Prominent mid-vein depressed above and protruding below.
*Internodes*.—0.50 to 1.50 cm in length.
*Foliar fragrance*.—Subtle resinous scent of lavender oil.
*Petiole*.—Sessile.
*Length*.—Approximately 3–4 cm in length.
*Width*.—0.50 cm in width.
Flower:
*Type of inflorescent*.—Terminal spike.
*Size of inflorescence*.—Short and compact 1–2 cm in width by 2.5–4 cm in length.
*Shape of inflorescence*.—Broad-conical.
*Peduncles*.—13–23 cm in height and 1 mm in width. Eramous with an occasional base whorl 1–2 cm below the main spike.
*Peduncle color*.—191A.
*Flower shape*.—Tubular.
*Corolla*.—Two-lipped with upper lip 2-lobed and lower lip 3-lobed.
*Corolla color*.—92A to 93C.
*Color of flower opening*.—91A.
*Calyx color*.—94B.
*Calyx surface*.—Pubescent.
*Bracteoles*.—Narrow, branched and 3 mm in length.
*Bud color*.—91B.
*Fragrance*.—Sweet.
*Blooming period*.—July and August.
Reproductive organs: Have not been observed.
Seed production: Not observed.

We claim:

1. A new and distinct variety of *Lavandula angustifolia* plant named 'Walvera' as described and illustrated.

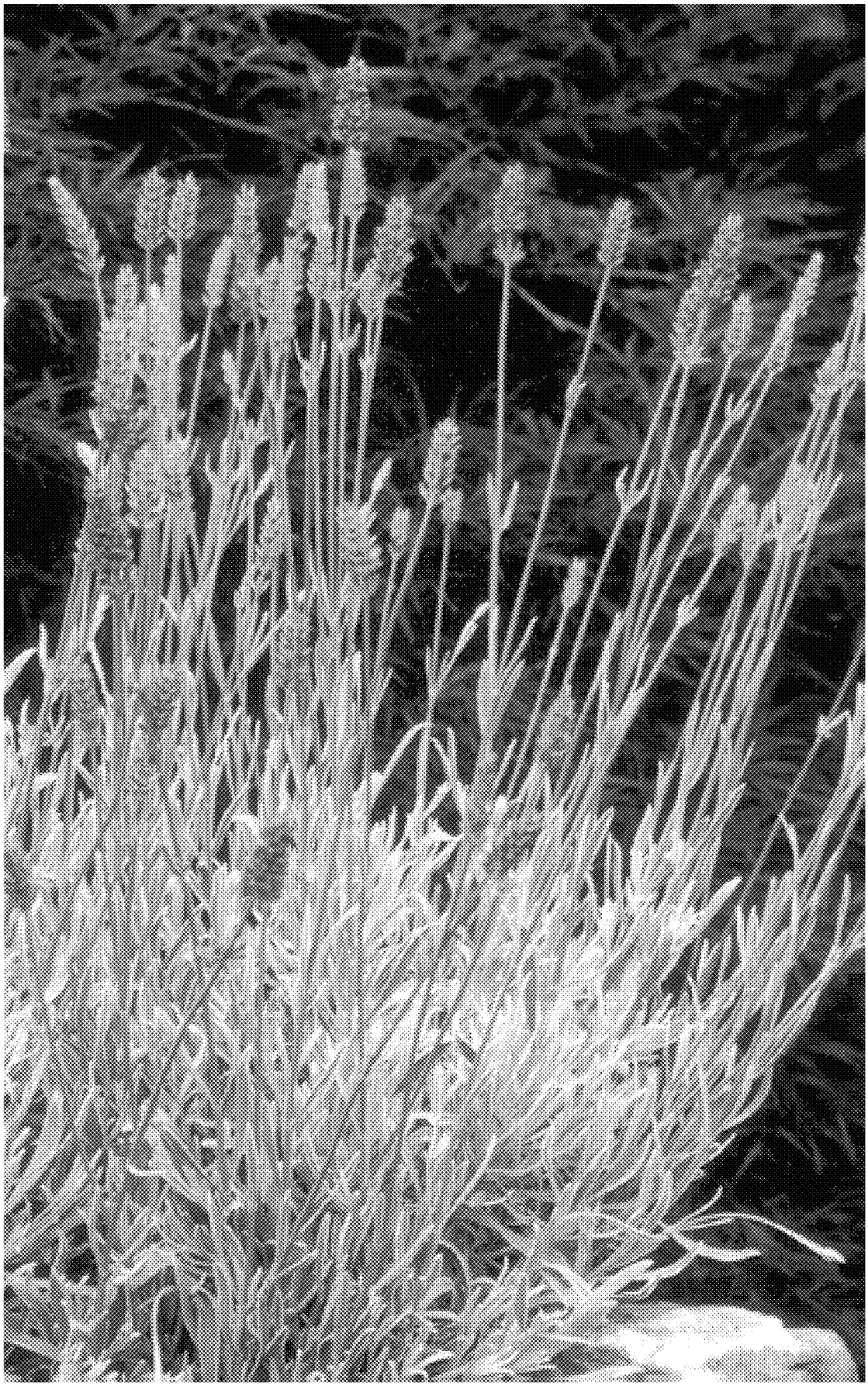

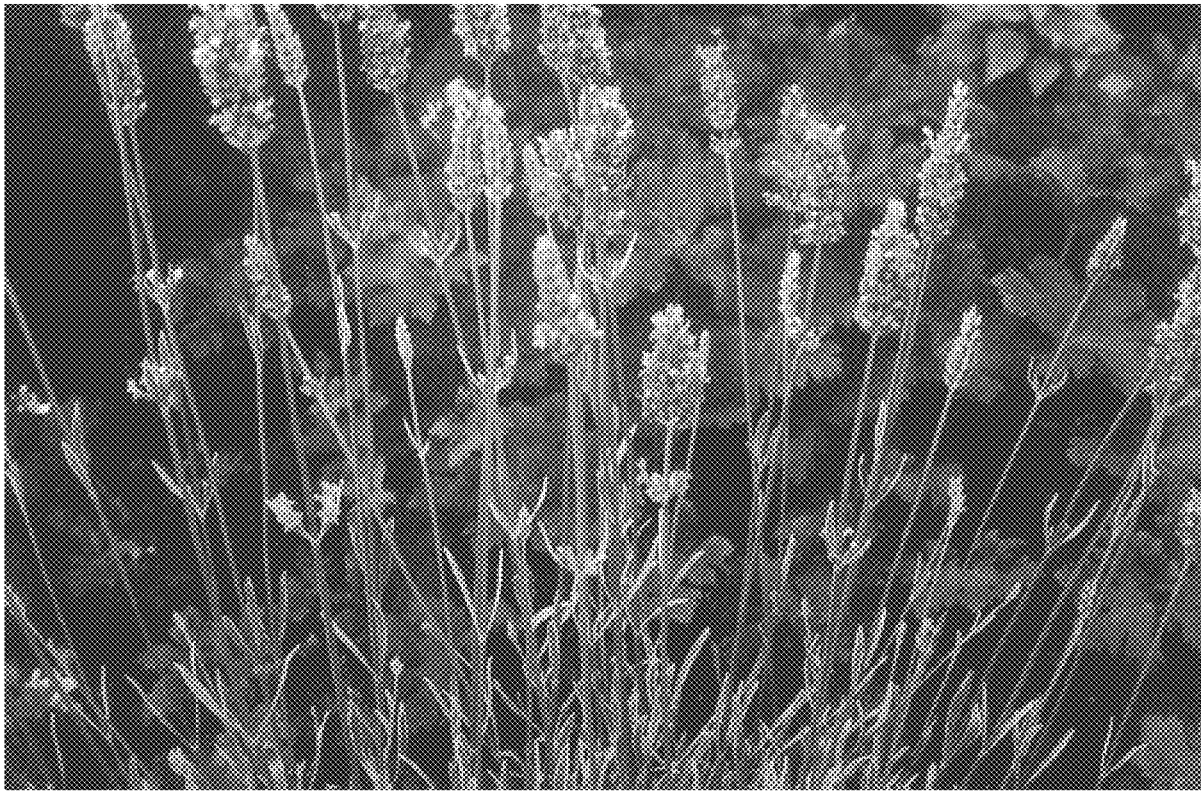

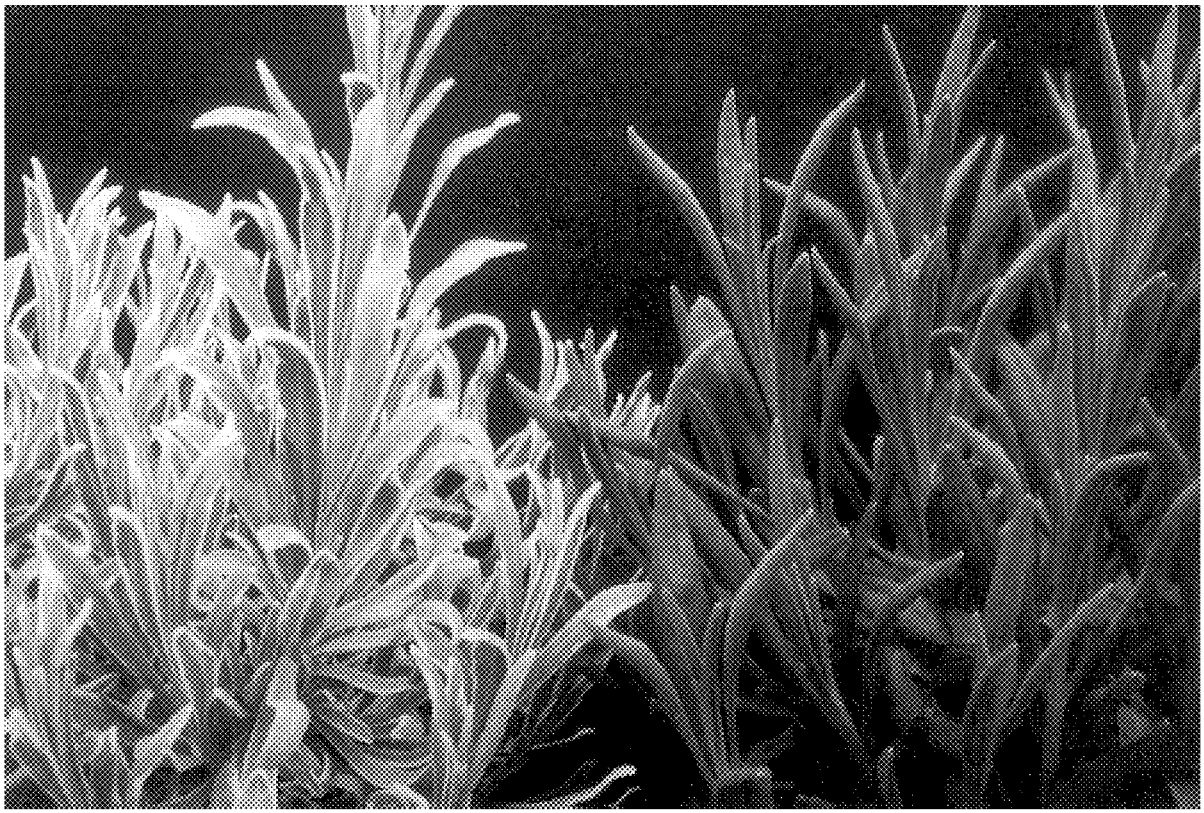

* * * * *